United States Patent [19]

Funatsu et al.

[11] Patent Number: 5,149,706
[45] Date of Patent: Sep. 22, 1992

[54] STABILIZED ISOTHIAZOLONE

[75] Inventors: Ryoji Funatsu, Tokyo; Susumu Mitsui, Koshigaya; Shigeru Kurose, Misato; Atsuko Gato, Koshigaya, all of Japan

[73] Assignee: Somar Corporation, Japan

[21] Appl. No.: 546,851

[22] Filed: Jul. 2, 1990

[30] Foreign Application Priority Data

Jul. 17, 1989 [JP] Japan .................................. 1-183924

[51] Int. Cl.$^5$ ..................... A61K 31/425; A61K 31/08
[52] U.S. Cl. ..................................... 514/372; 514/723; 514/970
[58] Field of Search .................. 514/372, 970, 723

[56] References Cited

U.S. PATENT DOCUMENTS 4,322,475  3/1982  Lewis et al. .................. 428/411
4,539,071  9/1985  Clifford et al. ................ 162/161

FOREIGN PATENT DOCUMENTS 0166611  2/1986  European Pat. Off. .
0194146  10/1986  European Pat. Off. .

OTHER PUBLICATIONS

CA 108(26): 222627x, Nagasawa et al., 1988.
CA 107(20): 187498m, Nogami et al., 1987.
CA: vol. 113, 1990, #23898q, Igarashi et al.
WPIL, FIle Supplier, JP-A-56099401, Oct. 8, 1981 (Whole abstract).
WPIL, File Supplier, JP-A-59 077859, Apr. 5, 1984 (Whole abstract).

*Primary Examiner*—Frederick E. Waddell
*Assistant Examiner*—Kimberly R. Jordan
*Attorney, Agent, or Firm*—Lorusso & Loud

[57] ABSTRACT

A germicidal composition is disclosed which comprises a solvent containing at least 50% by weight of a stabilizing liquid selected from 3-methyl-3-methoxybutyl alcohol and an isothiazolone compound dissolved in the solvent.

5 Claims, No Drawings

STABILIZED ISOTHIAZOLONE

This invention relates generally to a germicide suitable for preventing growth of various germs such as yeasts and filamentous fungi in industrial water such as waste water from pulp mills or cooling water for heat exchangers and, more specifically, to a germicidal composition of the above-mentioned type which is stable and has an improved shelf life.

In industrial water such as waste water from paper making steps in pulp-related industries and recirculating cooling water used in various mills, microorganisms such as germs, fungi and bacteria are apt to grow to form slimes which cause various problems. To cope with this, various germicides have been proposed and some of them are actually used for destroying germs or preventing growth of germs in various fields. Among various germicides, an isothiazolone compound is known to be especially effective in preventing the occurrence of slimes. Isothiazolone compound-containing germicides are generally stored, transported or placed on sales in the form of concentrated solutions. Glycols, ketones or ethers are generally used as solvents for such germicidal solutions.

It has been found, however, that isothiazolone compounds in such solutions are not stable and, therefore, the germicidal activity of such solutions is gradually degraded when stored for a long period of time.

The present invention has been made with the above problem of the conventional germicides in view and is contemplated to provide an isothiazolone-type germicide having an improved shelf life. In accordance with the present invention there is provided a composition in the form of a solution, comprising:

an isothiazolone compound; and a solvent containing at least 50% by weight of a stabilizing liquid having the following general formula:

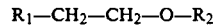

wherein $R_1$ stands for $-C(CH_3)_2OCH_3$ or $-OCOCH_3$ and $R_2$ stands for hydrogen or $-COCH_3$ with the proviso that when $R_1$ is $-C(CH_3)_2OCH_3$ $R_2$ is hydrogen and that when $R_1$ is $-OCOCH_3$ $R_2$ is $-COCH_3$.

The present invention will now be described in detail below.

Any isothiazolone compound may be used for the purpose of the present invention as long as it has a germicidal activity. If desired, a mixture of two or more isothiazolone compounds may be used. Particularly suited are isothiazolone compounds represented by the following general formula:

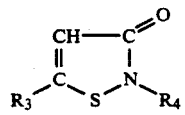

wherein $R_3$ stands for hydrogen or halogen and $R_4$ stands for hydrogen or alkyl. Illustrative of suitable isothiazolone compounds are 2-methyl-3-isothiazolone, 5-chloro-2-methyl-3-isothiazolone, 2-octyl-3-isothiazolone, 2-ethyl-3-isothiazolone and mixtures thereof. Complexes of isothiazolones, such as calcium chloride complexes, magnesium nitrate complexes and iron chloride complexes, may also be used, though the use of free form isothiazolones is preferred.

The present invention is characterized by using a specific stabilizing liquid as shown by the above general formula as a major component of a solvent for the above isothiazolone compounds. It is important that the solvent should contain at least 50% by weight, preferably 60% by weight of the stabilizing liquid in order to attain the object of the present invention.

If desired, an auxiliary organic solvent may be used in conjunction with the stabilizing liquid. Examples of such auxiliary solvents include monohydric alcohols such as benzyl alcohol, butanol and isopropyl alcohol; glycols such as ethylene glycol, diethylene glycol, triethylene glycol, polyethylene glycol and propylene glycol; ethers such as ethylene glycol mono(or di)alkyl ether, 1,4-dioxane, dibenzyl ether and propylene oxide; esters such as ethylene glycol monoacetate, alkyl acetates and alkyl adipates; hydrocarbons such as dodecylbenzene and psuedocumene, amides such as dimethylformamide; ketones such as methyl isobutyl ketone; and dimethylsulfoxide. The amount of such an auxiliary solvent should not exceed 50% by weight.

The solvent containing the above stabilizing liquid and, optionally, the above auxiliary solvent, is generally used in an amount so that the concentration of the isothiazolone compound is 0.1-70% by weight, preferably 0.4-50% by weight, based on the total weight of the isothiazolone compound and the solvent.

If desired, isothiazolone compounds may be used in conjunction with one or more other germicides such as 4,5-dichloro-1,2-dithiole-3-one, 2,2-dibromo-3-nitrilepropionamide, 2,2-dibromo-2-nitroethanol, methylenebisthiocyanate, 1-chlorobenzaldoxime acetate and bis(bromoacetoxy)butene.

Solutions of an isothiazolone compound in the above stabilizing liquid-containing solvent are excellent in stability and the isothiazolone compound in the solution is prevented from decomposing for a long period of time. Thus, degradation of germicidal activity during storage or transportation is effectively prevented, so that the solution is advantageously used as a germicide or a raw material for the production of germicides.

The following examples will further illustrate the present invention.

EXAMPLES 1-17

One or more of the isothiazolone compounds shown in Table 1 were dissolved in 3-methyl-3-methoxybutyl alcohol of the formula:

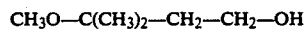

or a mixed solvent composed of 3-methyl-3-methoxybutyl alcohol and an auxiliary solvent shown in Table 1. The amounts (parts by weight) of the isothiazolone compounds, 3-methyl-3-methoxybutyl alcohol and the auxiliary solvents are also shown in Table 1.

In Table 1, the abbreviations are as follows:

Isothiazolone Compound
ITZ-1: 5-Chloro-2-methylisothiazolone
ITZ-2: 2-Methylisothiazolone
ITZ-3: 2-Octylisothiazolone Stabilizinq Liquid
MMB: 3-Methyl-3-methoxybutyl alcohol Auxiliary Solvent
EG: Ethylene glycol
DEG: Diethylene glycol PG: Propylene glycol
DGME: Diethylene glycol monomethyl ether
MBK: Methyl isobutyl ketone
DBE: Dibenzyl ether
PO: Propylene oxide
PEG: Polyethylene glycol (molecular weight: 400)

The thus prepared solutions were then allowed to stand at 40° C. for 30 days. The concentration (C) of the isothiazolone compound or compounds in each solution was measured 5, 10, 20 and 30 days after the preparation thereof to evaluate the stability thereof in terms of "survival rate" calculated from the following equation:

$$\text{Survival rate} = \frac{C}{C_0} \times 100\%$$

wherein C represents the measured concentration and $C_0$ represents the initial concentration. The results are also shown in Table 1.

amounts of 3-methyl-3-methoxybutyl alcohol and the auxiliary solvents were changed as shown in Table 2. The results are also summarized in Table 2.

EXAMPLES 18–34

Examples 1–17 were repeated in the same manner as described except that ethylene glycol diacetate (EGD) of the formula:

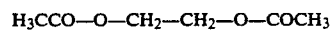

$$H_3CCO-O-CH_2-CH_2-O-COCH_3$$

was used as the stabilizing liquid in place of 3-methyl-3-methoxybutyl alcohol. The results are shown in Table 3.

COMPARATIVE EXAMPLES 18–25

Comparative Examples 10–17 were repeated in the same manner as described except that ethylene glycol diacetate (EGD) was used as the stabilizing liquid in

TABLE 1

| | Example No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Isothiazolone | | | | | | | | | | | | | | | | | |
| ITZ-1 | 20 | | | 15 | 20 | 20 | 20 | 20 | 20 | 20 | 20 | 20 | 15 | 15 | | 5 | 5 |
| ITZ-2 | | 20 | | 5 | | | | | | | | | 5 | 5 | | | |
| ITZ-3 | | | 20 | | | | | | | | | | | | 20 | | |
| Stabilizing Liquid | | | | | | | | | | | | | | | | | |
| MMB | 80 | 80 | 80 | 80 | 50 | 50 | 50 | 50 | 50 | 50 | 50 | 50 | 50 | 70 | 70 | 95 | 60 |
| Auxiliary Solvent | | | | | | | | | | | | | | | | | |
| EG | | | | | 30 | | | | | | | | 30 | 10 | | | 35 |
| DEG | | | | | | 30 | | | | | | | | | | | |
| PG | | | | | | | 30 | | | | | | | | 10 | | |
| DGME | | | | | | | | 30 | | | | | | | | | |
| MBK | | | | | | | | | 30 | | | | | | | | |
| DBE | | | | | | | | | | 30 | | | | | | | |
| PO | | | | | | | | | | | 30 | | | | | | |
| PEG | | | | | | | | | | | | 30 | | | | | |
| Survival Rate (%) | | | | | | | | | | | | | | | | | |
| 5 days | 100 | 100 | 100 | 100 | 100 | 100 | 100 | 100 | 100 | 100 | 100 | 100 | 100 | 100 | 100 | 100 | 100 |
| 10 days | 100 | 100 | 100 | 100 | 100 | 100 | 100 | 100 | 100 | 100 | 100 | 100 | 100 | 100 | 100 | 100 | 100 |
| 20 days | 100 | 100 | 100 | 100 | 98 | 98 | 95 | 98 | 93 | 96 | 98 | 98 | 98 | 100 | 100 | 100 | 99 |
| 30 days | 99 | 100 | 100 | 100 | 95 | 96 | 92 | 96 | 88 | 91 | 96 | 96 | 97 | 98 | 98 | 100 | 98 |

COMPARATIVE EXAMPLES 1–17

The procedures of the above examples were repeated in the same manner as described except that the place of 3-methyl-3-methoxybutyl alcohol. The results are shown in Table 4 together with those of Comparative Examples 1–9.

TABLE 2

| | Comparative Example No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Isothiazolone | | | | | | | | | | | | | | | | | |
| ITZ-1 | 20 | | | 15 | 20 | 20 | 20 | 20 | 20 | 20 | 20 | 20 | 15 | 15 | | 5 | 5 |
| ITZ-2 | | 20 | | 5 | | | | | | | | | 5 | 5 | | | |
| ITZ-3 | | | 20 | | | | | | | | | | | | 20 | | |
| Stabilizing Liquid | | | | | | | | | | | | | | | | | |
| MMB | | | | | | | | | | 30 | 30 | 30 | 30 | 10 | 10 | | 10 |
| Auxiliary Solvent | | | | | | | | | | | | | | | | | |
| EG | 80 | 80 | | | | | | | | 50 | | | 50 | 70 | | 95 | 85 |
| DEG | | | | 80 | | | | | | | | | | | | | |
| PG | | | 80 | | | | | | | | | | | | 70 | | |
| DGME | | | | | 80 | | | | | | | 50 | | | | | |
| MBK | | | | | | 80 | | | | | | | | | | | |
| DBE | | | | | | | 80 | | | | | | 50 | | | | |
| PO | | | | | | | | 80 | | | | | | | | | |
| PEG | | | | | | | | | 80 | | | | | | | | |
| Survival Rate (%) | | | | | | | | | | | | | | | | | |
| 5 days | 86 | 99 | 100 | 98 | 85 | 65 | 85 | 50 | 63 | 98 | 96 | 100 | 100 | 96 | 100 | 90 | 100 |

TABLE 2-continued

| | Comparative Example No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| 10 days | 75 | 88 | 96 | 80 | 24 | 16 | 80 | 2 | 8 | 86 | 86 | 76 | 90 | 82 | 92 | 66 | 90 |
| 20 days | 69 | 54 | 65 | 65 | 13 | 5 | 52 | 0 | 0 | 70 | 75 | 46 | 32 | 26 | 62 | 34 | 62 |
| 30 days | 3 | 25 | 45 | 12 | 2 | 0 | 9 | 0 | 0 | 6 | 3 | 2 | 0 | 0 | 21 | 6 | 10 |

TABLE 3

| | Example No. | | | | | | | | | | | | | | | | |
|---|---|---|---|---|---|---|---|---|---|---|---|---|---|---|---|---|---|
| | 18 | 19 | 20 | 21 | 22 | 23 | 24 | 25 | 26 | 27 | 28 | 29 | 30 | 31 | 32 | 33 | 34 |
| Isothiazolone | | | | | | | | | | | | | | | | | |
| ITZ-1 | 20 | | | 15 | 20 | 20 | 20 | 20 | 20 | 20 | 20 | 20 | 20 | 15 | 15 | | 5 | 5 |
| ITZ-2 | | 20 | | 5 | | | | | | | | | | 5 | 5 | | | |
| ITZ-3 | | | 20 | | | | | | | | | | | | | 20 | | |
| Stabilizing Liquid | | | | | | | | | | | | | | | | | |
| MMB | 80 | 80 | 80 | 80 | 50 | 50 | 50 | 50 | 50 | 50 | 50 | 50 | 50 | 70 | 70 | 95 | 60 |
| Auxiliary Solvent | | | | | | | | | | | | | | | | | |
| EG | | | | | 30 | | | | | | | | 30 | 10 | | | 35 |
| DEG | | | | | | 30 | | | | | | | | | | | |
| PG | | | | | | | 30 | | | | | | | | 10 | | |
| DGME | | | | | | | | 30 | | | | | | | | | |
| MBK | | | | | | | | | 30 | | | | | | | | |
| DBE | | | | | | | | | | 30 | | | | | | | |
| PO | | | | | | | | | | | 30 | | | | | | |
| PEG | | | | | | | | | | | | 30 | | | | | |
| Survival Rate (%) | | | | | | | | | | | | | | | | | |
| 5 days | 100 | 100 | 100 | 100 | 100 | 100 | 100 | 100 | 100 | 100 | 100 | 100 | 100 | 100 | 100 | 100 | 100 |
| 10 days | 100 | 100 | 100 | 100 | 100 | 100 | 100 | 100 | 100 | 100 | 100 | 100 | 100 | 100 | 100 | 100 | 100 |
| 20 days | 100 | 100 | 100 | 100 | 100 | 100 | 98 | 100 | 93 | 98 | 100 | 100 | 100 | 100 | 100 | 100 | 99 |
| 30 days | 99 | 100 | 100 | 100 | 95 | 96 | 92 | 96 | 90 | 93 | 98 | 98 | 97 | 98 | 98 | 98 | 98 |

TABLE 4

| | Comparative Example No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 18 | 19 | 20 | 21 | 22 | 23 | 24 | 25 |
| Isothiazolone | | | | | | | | | | | | | | | | | |
| ITZ-1 | 20 | | | 15 | 20 | 20 | 20 | 20 | 20 | 20 | 20 | 20 | 15 | 15 | | 5 | 5 |
| ITZ-2 | | 20 | | 5 | | | | | | | | | 5 | 5 | | | |
| ITZ-3 | | | 20 | | | | | | | | | | | | 20 | | |
| Stabilizing Liquid | | | | | | | | | | | | | | | | | |
| EGD | | | | | | | | | | 30 | 30 | 30 | 30 | 10 | 10 | | 10 |
| Auxiliary Solvent | | | | | | | | | | | | | | | | | |
| EG | 80 | 80 | | | | | | | | | 50 | | 50 | 70 | | 95 | 85 |
| DEG | | | | 80 | | | | | | | | | | | | | |
| PG | | | 80 | | | | | | | | | | | 70 | | | |
| DGME | | | | | 80 | | | | | | | 50 | | | | | |
| MBK | | | | | | 80 | | | | | | | | | | | |
| DBE | | | | | | | 80 | | | | | | 50 | | | | |
| PO | | | | | | | | 80 | | | | | | | | | |
| PEG | | | | | | | | | 80 | | | | | | | | |
| Survival Rate (%) | | | | | | | | | | | | | | | | | |
| 5 days | 86 | 99 | 100 | 98 | 85 | 65 | 85 | 50 | 63 | 96 | 96 | 96 | 96 | 100 | 100 | 90 | 96 |
| 10 days | 75 | 88 | 96 | 80 | 24 | 16 | 80 | 2 | 8 | 80 | 90 | 74 | 86 | 88 | 88 | 66 | 82 |
| 20 days | 69 | 54 | 65 | 65 | 13 | 5 | 52 | 0 | 0 | 62 | 70 | 40 | 36 | 36 | 52 | 34 | 50 |
| 30 days | 3 | 25 | 45 | 12 | 2 | 0 | 9 | 0 | 0 | 2 | 4 | 0 | 0 | 0 | 10 | 6 | 6 |

We claim:

1. A stabilized isothiazolone germicidal composition comprising consisting essentially of:
   a solvent containing at least 50% by weight of 3-methyl-3-methoxybutyl alcohol; and
   an isothiazolone compound dissolved in said solvent.

2. A composition according to claim 1, wherein the isothiazolone compound is present in an amount of 0.1–70% by weight of the composition.

3. A composition according to claim 1, wherein said isothiazolone compound is at least one compound selected from those represented by the following general formula:

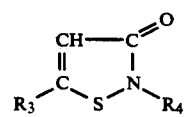

wherein $R_3$ stands for hydrogen or halogen and $R_4$ stands for hydrogen or alkyl, and complexes thereof.

4. A composition according to claim 1, wherein the content of said 3-methyl-3-methoxybutyl alcohol in said solvent is at least 60% by weight.

5. A composition according to claim 1, further comprising consisting essentially of one or more germicide selected from the group consisting of 4,5-dichloro-1,2-dithiole-3-one, 2,2-dibromo-3-nitrilepropionamide, 2,2-dibromo-2-nitroethanol, methylenebisthiocyanate, 1-chlorobenzaldoxime acetate and bis(bromoacetoxy)butene.

* * * * *

UNITED STATES PATENT AND TRADEMARK OFFICE
CERTIFICATE OF CORRECTION

PATENT NO. : 5,149,706
DATED : September 22, 1992
INVENTOR(S) : FUNATSU et al

It is certified that error appears in the above-identified patent and that said Letters Patent is hereby corrected as shown below:

IN THE CLAIMS:

Col. 5, line 60, delete "comprising".

Col. 7, line 4, delete "com-"; and line 5, delete "prising".

Signed and Sealed this

Twenty-sixth Day of October, 1993

Attest:

BRUCE LEHMAN

Attesting Officer     Commissioner of Patents and Trademarks